United States Patent [19]

Deutch et al.

[11] Patent Number: 5,426,100

[45] Date of Patent: Jun. 20, 1995

[54] PIPTIDE FRAGMENTS AND ANALOGS OF THROMBOSPONDIN

[75] Inventors: Alan H. Deutch, Columbia, Md.; Goerge Tuszynski, Mays Landing, N.J.

[73] Assignees: W. R. Grace & Co.-Conn., New York, N.Y.; Medical College of PA, Philadephia, Pa.

[21] Appl. No.: 110,146

[22] Filed: Aug. 20, 1993

Related U.S. Application Data

[60] Continuation of Ser. No. 896,527, Jun. 9, 1992, abandoned, which is a division of Ser. No. 483,527, Feb. 22, 1990, Pat. No. 5,190,918.

[51] Int. Cl.[6] .................... A61K 37/00; A61K 37/02; C07K 5/00; C07K 7/00
[52] U.S. Cl. ......................... 514/15; 514/12; 514/13; 514/14; 530/324; 530/325; 530/326; 530/327
[58] Field of Search ............. 514/12, 13, 14, 15; 530/324, 325, 326, 327

[56] References Cited

U.S. PATENT DOCUMENTS 5,192,744 3/1993 Bouck et al. .................. 514/8

OTHER PUBLICATIONS

Lawler et al., vol. 13, No. 3, Seminars in Thrombosis and Hemostasis, 1987.
Robson et al., vol. 335, Nature, 1 Sep. 1988.

*Primary Examiner*—Robert J. Hill, Jr.
*Assistant Examiner*—A. M. Davenport
*Attorney, Agent, or Firm*—Bharat C. Gandhi

[57] ABSTRACT

Compounds and compositions comprising fragments and synthetic analogs of human thrombospondin are provided together with methods for their use as thrombospondin-like agents.

9 Claims, 1 Drawing Sheet

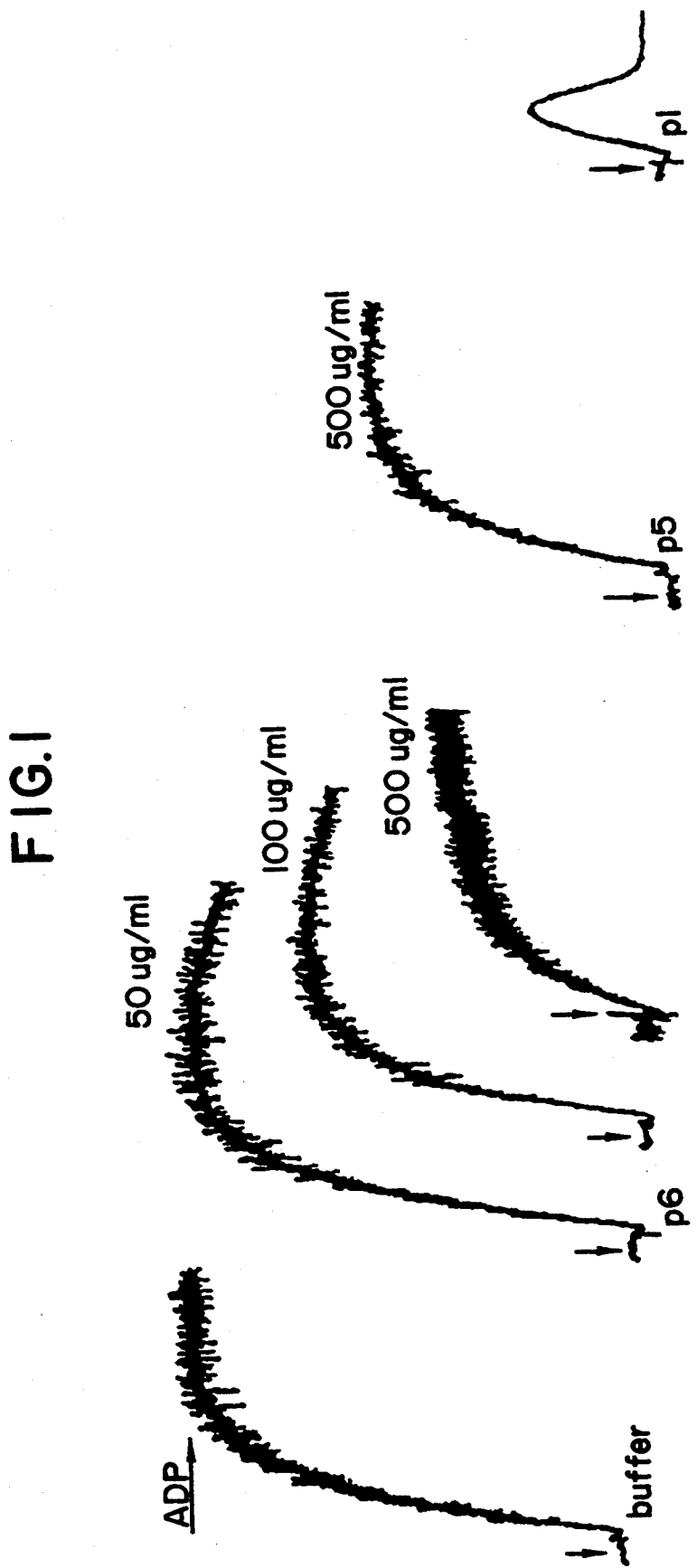

PIPTIDE FRAGMENTS AND ANALOGS OF THROMBOSPONDIN

This is a continuation of application Ser. No. 07/896,527, filed Jun. 9, 1992 and now abandoned which is a division of application Ser. No. 438,527, filed Feb. 22, 1990 and now U.S. Pat. No. 5,190,918.

TECHNICAL FIELD

The present invention relates generally to peptide fragments and synthetic analogs of thrombospondin which retain thrombospondin-like-activity. The peptides find use as agents in anti-tumor development, wound healing, atherosclerosis, antimalaria, antithrombotics, thrombolytics, angiogenesis, complement activation, cell attachment, diagnostic reagents and other related areas.

BACKGROUND

Thrombospondin (also known as thrombin sensitive protein or TSP) is a large molecular weight 180 kD glycoprotein composed of three identical disulfide-linked polypeptide chains. Thrombospondin has been purified by a number or procedures including exclusion chromatography (Lawler et al., *J. Biol. Chem.* (1978) 253:8609-16), heparin affinity chromatography (Lawler et al., *Thromb. Res.* (1981) 22:267-269), fibrinogen affinity chromatography (Tuszynski et al., *J. Biol. Chem.* (1985) 260:12240-5), barium chloride precipitation (Alexander et al., *Biochem. J.* (1984) 217:67-71) and anion exchange chromatography with HPLC (Clezarolin et al., *J. Chromatog.* (1984) 296:249-56).

The complete amino acid sequence of TSP has been deduced from DNA clones prepared by various groups including Lawler et al., *J. Cell Biol.* (1986) 103:1635-48; Kobayashi et al., *Biochemistry* (1986) 25:8418-25; Dixit et al., *Proc. Ntl. Acad. Sci.* (1986) 83:5449-53; and Hennessy et al., *J. Cell Biol.* (1989) 108: 729-36.

Kobayashi et al. (supra), Robson et al. (*Nature* (1988) 335:79-82) and Goundis et al. (*Nature* (1988) 335:82-85) compared the sequences of thrombospondin, thrombospondin-related anonymous protein, properdin, the terminal complement components, and circumsporozoite proteins and recognized a significant homology based around the consensus sequence W-S-P-C-S-V-T-C-G. While the sequence homology was recognized, there was no known use for such sequence.

The present invention provides thrombospondin fragments and analogs which mimic or inhibit the biological activity of intact thrombospondin which find use in a variety of biological, prophylactic or therapeutic areas.

SUMMARY OF THE INVENTION

It has now been found that a class of fragments or synthetic analogs of thrombospondin have a variety of uses. These peptides are capable of inhibiting tumor metastasis in mammals in vivo. The peptides are also useful in wound healing, atherosclerosis, malaria, thrombotic, and thrombolytic conditions, angiogenesis, and as cell attachment promoters, complement modulators, and diagnostic reagents and in other related areas. Analogs based on the Type I repeat of thrombospondin described by Lawler et al., (*Seminars in Thrombosis & Hemostasis* (1987) 13:245-254), Robson et al., Supra, and Groundis et al., supra, have been shown to have thrombospondin-like activity. Specifically, analogs based around and including at least a portion of the sequence motif of Robson (supra) W-S-P-C-S-V-T-C-G have been shown to have thrombospondin-like activity.

The present invention is, therefore, in one aspect directed to polypeptide compounds having thrombospondin-like activity which are identified by the formula:

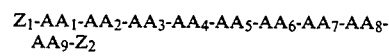

$Z_1$-$AA_1$-$AA_2$-$AA_3$-$AA_4$-$AA_5$-$AA_6$-$AA_7$-$AA_8$-$AA_9$-$Z_2$ wherein:

- $AA_1$ is a neutral/non-polar/large/cyclic amino acid residue;
- $AA_2$ is a neutral/polar/small or neutral/polar/large/non-cyclic or acidic amino acid residue;
- $AA_3$ is a neutral/nonpolar/large/cyclic or neutral/non-polar/large/non-cyclic or neutral/polar/large/non-cyclic or neutral/polar/small amino acid residue;
- $AA_4$ is a neutral/polar/small amino acid residue;
- $AA_5$ is a neutral/polar/small or neutral/polar/large/non-cyclic amino acid residue;
- $AA_6$ is a neutral/nonpolar/large/non-cyclic or neutral/polar/large/non-cyclic amino acid residue;
- $AA_7$ is a neutral/polar/large/non-cyclic or neutral/polar/small amino acid residue;
- $AA_8$ is a neutral/polar/small amino acid residue;
- $AA_9$ is a neutral/polar/small amino acid residue;
- $Z_1$ is hydrogen, amino, acetyl or at least one amino acid residue or the desamino form thereof;
- $Z_2$ is hydroxyl, carboxyl, non-amino acids such as agmatine, or at least one amino acid residue, including carboxyamide or alkylamide forms thereof.

Also provided in accordance with aspects of the invention are pharmaceutical compositions which contain the above-recited polypeptide compounds together with a pharmaceutically acceptable liquid, gel or solid carrier. Administration of therapeutically effective doses of these compositions can provide effective enhancement or inhibition of thrombospondin-like activity to animals, particularly vertebrates such as mammalian and avian hosts.

BRIEF DESCRIPTION OF THE DRAWINGS

FIG. 1 depicts the in vitro ability of selected peptide compounds of the present invention to inhibit platelet aggregation.

DETAILED DESCRIPTION OF THE INVENTION

In accordance with the present invention, a class of fragments and analogs of thrombospondin is provided which is capable of inhibiting or mimicing the activity of thrombospondin in mammals in vivo.

A. Definitions

"Thrombospondin-like activity" is defined herein as any activity that mimics the known biological activities of thrombospondin. These activities include cell-adhesion promoting activity, cell mitogenic activity, cell chemotactic activities, and hemostatic activities and any activities that derive from these activities such as tumor cell, microbial, or parasite metastasis activity, platelet aggregating activity, fibrinolytic activity and immune modulation.

"Antimetastatic activity" is defined herein as the ability to prevent or greatly reduce the extent or size of tumor cell metastasis, or inhibit or cause regression of primary solid tumors.

"Wound healing activity" is defined herein as the ability to increase the rate at which wounds heal or to improve the results of the healing process (i.e., less scarring, good response to tactile stimulus, etc.)

"Atherosclerosis activity" is defined herein as the capacity of thrombospondin to either promote or inhibit atherosclerotic lesion formation. The atherosclerotic lesion is defined as the degenerative accumulation of lipid-containing materials, especially in arterial walls.

"Antimalaria activity" is defined herein as the ability to inhibit either the cytoadherence of malarial-infected red blood cells to endothelial cells, the malarial sporozoite recognition and entry into hepatocytes, or the malarial merozoite recognition and entry into red blood cells. Antimalarial activity can be demonstrated in the form of a vaccine or a therapeutic that blocks cytoadherence.

"Antithrombotic activity" is defined herein as the ability to either inhibit the aggregation of platelets or to antagonize the formation of a thrombus.

"Thrombolytic activity" is defined herein as the ability to disrupt the structure of a thrombus.

"Angiogenesis activity" is defined herein as the ability to inhibit or enhance the formation of blood vessels or lymph vessels.

"Growth factor activity" is defined herein as the ability to inhibit or promote cell proliferation.

"Cell adhesion activity" is defined herein as the ability to promote or inhibit the attachment of cells, preferably mammalian cells, to a substrate.

"Complement activity" is defined herein as the ability to activate or block the Complement Cascade Pathway of the immune system.

"Antiviral activity" is defined herein as the ability to prevent or inhibit viral infection by interfering with the ability of the viral particle to bind to cells.

The sequence of amino acid residues of the present polypeptide compounds, the core nonapeptide, and preferred embodiments thereof, are defined in terms of amino acids of certain characteristics of particular subclasses.

Amino acid residues can be generally subclassified into four major subclasses as follows:

Acidic, i.e., the residue has a negative charge due to loss of H ion at physiological pH and the residue is attracted by aqueous solution so as to seek the surface positions in the conformation of a peptide in which it is contained when the peptide is in aqueous medium.

Basic, i.e., the residue has a positive charge due to association with H ion at physiological pH and the residue is attracted by aqueous solution so as to seek the surface positions in the conformation of a peptide in which it is contained when the peptide is in aqueous medium.

Neutral/non-polar, i.e., the residues are not charged at physiological pH and the residue is repelled by aqueous solution so as to seek the inner positions in the conformation of a peptide in which it is contained when the peptide is in aqueous medium.

Neutral/polar, i.e., the residues are not charged at physiological pH and the residue is attracted by aqueous solution so as to seek the outer positions in the conformation of a peptide in which it is contained when the peptide is in aqueous medium.

It is understood, of course, that in a statistical collection of individual residue molecules some molecules will be charged, and some not. To fit the definition of charged, a significant percentage (at least approximately 25%) of the individual molecules are charged at physiological pH.

Amino acid residues can be further subclassified as cyclic or non-cyclic, a self-explanatory classification with respect to the side chain substituent groups of the residues, and as small or large. The residue is considered small if it contains a total of three carbon atoms or less. Small residues are, of course, always non-cyclic. For the naturally occurring protein amino acids, subclassification according to the foregoing scheme is as follows:

Acidic: Aspartic acid and Glutamic acid;
Basic/non-cyclic: Arginine and Lysine;
Basic/cyclic: Histidine;
Neutral/polar/small: Glycine, Serine and Cysteine;
Neutral/polar/large/non-cyclic: Threonine, Asparagine and Glutamine;
Neutral/polar/large/cyclic: Tyrosine;
Neutral/non-polar/small: Alanine;
Neutral/non-polar/large/non-cyclic: Valine, Isoleucine, Leucine and Methionine;
Neutral/non-polar/large/cyclic: Phenylalanine and Tryptophan.

The protein amino acid proline, although within the classification neutral/non-polar/large/cyclic, is not included as an alternative due to its known effects on the secondary conformation of peptide chains.

Certain commonly encountered non-natural amino acids, such as desamino Tyrosine (des Tyr), agmatine (Agm), n-formyl tryptophan (f-Trp), alpha-aminoisobutyric acid (Aib), and sarcosine (Sar), statine, ornithine (Orn), homolysine, homoserine, homoarginine, norleucine (Nle), norvaline may also be incorporated into the compounds of the invention. Desamino tyrosine is incorporated at the N-terminus. Agmatine and statine are incorporated at the C-terminus. Based on the above definition, n-formyl Trp is neutral/non-polar/large/cyclic, Sar is neutral/non-polar/small, Aib is neutral/non-polar/non-cyclic, Orn is basic/non-cyclic, homolysine is basic/non-cyclic, homoserine is neutral/polar/small, homoarginine is basic/non-cyclic, norleucine is neutral/non-polar/large/non-cyclic, and norvaline is neutral/non-polar/large/non-cyclic.

The nomenclature used to describe polypeptide compounds of the present invention follows the conventional practice wherein the amino group is presented to the left and the carboxy group to the right of each amino acid residue. In the formulae representing selected specific embodiments of the present invention, the amino- and carboxy-terminal groups, although not specifically shown, will be understood to be in the form they would assume at physiologic pH values, unless otherwise specified. In the amino acid structure formulae, each residue is generally represented by a single letter designation, corresponding to the trivial name of the amino acid, in accordance with the following schedule:

| Amino Acid | One-letter Symbol |
|---|---|
| Alanine | A |
| Arginine | R |
| Asparagine | N |
| Aspartic acid | D |
| Cysteine | C |

-continued

| Amino Acid | One-letter Symbol |
| --- | --- |
| Glutamine | Q |
| Glutamic acid | E |
| Glycine | G |
| Histidine | H |
| Isoleucine | I |
| Leucine | L |
| Lysine | K |
| Methionine | M |
| Phenylalanine | F |
| Proline | P |
| Serine | S |
| Threonine | T |
| Tryptophan | W |
| Tyrosine | Y |
| Valine | V |

In the present application, the L-form of any amino acid residue having an optical isomer is intended unless otherwise expressly indicated, e.g., by the symbol "[D-$AA_n$]."

Compounds within the scope of the present invention can be obtained by modifying the disclosed formulae in numerous ways, while preserving the activity of the polypeptide compounds thus obtained. For example, while the amino acids of these compounds are normally in the natural L optical isomer form, one or more, usually two or less and preferably one amino acid may be replaced with the optical isomer D form, or a D,L-racemic mixture can be provided in the molecules comprising the polypeptide compound. Additionally, a disulfide linkage may be present or absent in the compounds of the invention, as long as activity is maintained.

Amino acid residues contained within the compounds, and particularly at the carboxy- or amino-terminus, can also be modified by methylation, amidation, acetylation or substitution with other chemical groups which can, for example, change the circulating half-life, resistance to proteases and solubility of the compounds without adversely effecting their activity.

In addition to the preceding definitions, the following abbreviations have been used throughout in describing the invention:

| | |
| --- | --- |
| BCA | bicinchoninic acid |
| BSA | bovine serum albumin |
| t-Boc | t-butyloxycarbonyl |
| Bzl | benzyl |
| °C. | degrees centigrade |
| DCM | dichloromethane |
| DIEA | diisopropyl ethyl amine |
| DMEM | Dulbecco's minimum essential medium |
| DMF | dimethyl formamide |
| HF | hydrogen fluoride |
| HOBT | 1-hydroxybenzotriazole |
| HPLC | high performance liquid chromatography |
| mBHA | methylbenzhydrylamine |
| μg | micrograin |
| μl | microliter |
| ml | milliliter |
| mM | millimolar |
| nm | nanometers |
| NMP | N-methylpyrrolidone |
| % | percent |
| PAM | phenylacetamidomethyl |
| PBS | phosphate buffered saline |
| TFA | trifluoroacetic acid |

B. Preferred Embodiments

The polypeptide compounds of the invention all contain the core nonapeptide sequence:

$$Z_1\text{-}AA_1\text{-}AA_2\text{-}AA_3\text{-}AA_4\text{-}AA_5\text{-}AA_6\text{-}AA_7\text{-}AA_8\text{-}AA_9\text{-}Z_2$$

wherein:

$AA_1$ is a neutral/nonpolar/large/cyclic amino acid residue;

$AA_2$ is a neutral/polar/small or neutral/polar/large/-non-cyclic or acidic amino acid residue;

$AA_3$ is a neutral/nonpolar/large/cyclic or neutral/-nonpolar/large/non-cyclic or neutral/polar/large/non-cyclic or neutral/polar/small amino acid residue;

$AA_4$ is a neutral/polar/small amino acid residue;

$AA_5$ is a neutral/polar/small or neutral/polar/large/-non-cyclic amino acid residue;

$AA_6$ is a neutral/nonpolar/large/non-cyclic neutral/-polar/large/non-cyclic amino acid residue;

$AA_7$ is a neutral/polar/large/non-cyclic or neutral/-polar/small amino acid residue;

$AA_8$ is a neutral/polar/small amino acid residue $AA_9$ is a neutral/polar/small amino acid residue;

$Z_1$ is hydrogen, amino, acetyl or at least one amino acid residue or the desamino form thereof; and $Z_2$ is hydroxyl, carboxyl, non-amino acids such as agmatine, or at least one amino acid residue, including carboxyamide or alkylamide forms thereof.

The most preferred sequence of this core nonapeptide is W-S-P-C-S-V-T-C-G. Other preferred embodiments include polypeptide compounds wherein:

$AA_1$ is tryptophan or n-formyl-tryptophan;

$AA_2$ is serine, threonine or aspartic acid;

$AA_3$ is proline, glutamic acid, serine or isoleucine;

$AA_4$ is cysteine;

$AA_5$ is serine or asparagine;

$AA_6$ is valine or threonine;

$AA_7$ is threonine or serine;

$AA_8$ is cysteine;

$AA_9$ is glycine or serine, including carboxyamide forms thereof.

Particularly preferred are those embodiments wherein the sequence is selected from the group consisting of:

| Compound | Structure |
| --- | --- |
| p1 | W-S-P-C-S-V-T-C-G |
| p5 | fW-S-P-C-S-V-T-C-G |
| p6 | W-S-P-C-S-V-T-C-G-NH$_2$ |
| p18 | W-D-I-C-S-V-T-C-G |
| p19 | W-S-S-C-S-V-T-C-G |
| p20 | W-T-S-C-S-T-S-C-G |
| p11 | W-S-P-W-S-E-W-T-S-C-S-T-S-C-G-N-G-I-Q-Q-R-G-R |
| p17 | W-S-H-W-S-P-W-S-S-C-S-V-T-C-G-D-G-V-I-T-R-I-R |
| p12 | W-G-P-W-S-P-W-D-I-C-S-V-T-C-G-G-G-V-Q-K-R-S-R |
| | W-S-P-C-S-V-T-C-S |
| | W-S-Q-C-S-V-T-C-G |
| | W-S-Q-C-N-V-T-C-G |
| | W-T-P-C-S-V-T-C-G |
| p4 | D-G-G-W-S-H-W-S-P-W-S-S-C-S-V-T-C-G-D-G-V-I-T-R-I-R-L-C-N-S-P-S-P-Q-M-N-G-K-P-C-E-G-E-A-R-E-T-K-A-C-K-K-D-A-C-P-I-N-G-G |

Compounds within the scope of the present invention can be synthesized chemically by means well known in the art such as, e.g., solid phase peptide synthesis. The synthesis is commenced from the carboxy-terminal end of the peptide using an alpha-amino protected amino acid. t-Butylocarbonyl (Boc) protective groups can be used for all amino groups even though other protective groups are suitable. See Stewart et al., "Solid-Phase Peptide Synthesis," W. H. Freeman Co., San Francisco (1969) and Merrifield, *J. Am. Chem. Soc.* 85:2149-2154 (1963). These and other methods of peptide synthesis are also exemplified by U.S. Pat. Nos. 3,862,925, 3,842,067, 3,972,859 and 4,105,602.

Conveniently, compounds may be synthesized using manual techniques or automatically employing, for example, an Applied BioSystems 430A Peptide Synthesizer (Foster City, Calif.) or a Biosearch SAM II automatic peptide synthesizer (Biosearch, Inc., San Rafael, Calif.), following the instructions provided in the instruction manual supplied by the manufacturer.

It will be readily appreciated by those having ordinary skill in the art of peptide synthesis that the intermediates which are constructed in accordance with the present disclosure during the course of synthesizing the present compounds are themselves useful compounds and are thus within the scope of the invention.

Alternatively, selected compounds of the present invention can be produced by expression of recombinant DNA constructs prepared in accordance with well-known methods. Such production can be desirable to provide large quantities or alternative embodiments of such compounds.

C. Administration

Compounds of the present invention have thrombospondin-like activity in the intact animal. Compounds of the present invention and compositions containing them which are shown to have the physiological effect of inhibiting or mimicing the effect of intact thrombospondin find use in numerous therapeutic and prophylactic applications, such as cancer therapy, wound healing, atherosclerosis, malaria treatment or prevention, thrombotic or thrombolytic conditions, angiogenesis, complement activation, or cell attachment.

Thus the present invention also provides compositions containing an effective amount of compounds of the present invention, including the nontoxic addition salts, amides and esters thereof, which may, alone, serve to provide the above-recited therapeutic benefits. Such compositions can also be provided together with physiologically tolerable liquid, gel or solid diluents, adjuvants and excipients.

These compounds and compositions can be administered to animals for veterinary use, such as with domestic animals, and clinical use in humans in a manner similar to other therapeutic agents. In general, the dosage required for therapeutic efficacy will range from about 1 ug to 300 mg/kg, more usually 10 $\mu$g to 30 mg/kg of the host body weight. Alternatively, dosages within these ranges can be administered by constant infusion over an extended period of time, usually exceeding 24 hours, until the desired therapeutic benefits have been obtained.

Typically, such compositions are prepared as injectables, either as liquid solutions or suspensions; solid forms suitable for solution in, or suspension in, liquid prior to injection may also be prepared. The preparation may also be emulsified. The active ingredient is often mixed with diluents or excipients which are physiologically tolerable and compatible with the active ingredient. Suitable diluents and excipients are, for example, water, saline, dextrose, glycerol, or the like, and combinations thereof. In addition, if desired, the compositions may contain minor amounts of auxiliary substances such as wetting or emulsifying agents, stabilizing or pH buffering agents, and the like.

The compositions are conventionally administered parenterally, by injection, for example, either subcutaneously or intravenously. Additional formulations which are suitable for other modes of administration include suppositories, intranasal aerosols, and, in some cases, oral formulations. For suppositories, traditional binders and excipients may include, for example, polyalkylene glycols or triglycerides: such suppositories may be formed from mixtures containing the active ingredient in the range of 0.5% to 10%, preferably 1%-2%. Oral formulations include such normally employed excipients as, for example, pharmaceutical grades of mannitol, lactose, starch, magnesium stearate, sodium saccharin, cellulose, magnesium carbonate, and the like. These compositions take the form of solutions, suspensions, tablets, pills, capsules, sustained release formulations, or powders, and contain 10%-95% of active ingredient, preferably 25%-70%. These oral formulations include formulations designed to protect the peptide until it can be absorbed.

The peptide compounds may be formulated into the compositions as neutral or salt forms. Pharmaceutically acceptable non-toxic salts include the acid addition salts (formed with the free amino groups) and which are formed with inorganic acids such as, for example, hydrochloric or phosphoric acids, or such organic acids as acetic, oxalic, tartaric, mandelic, and the like. Salts formed with the free carboxyl groups may be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

In addition to the compounds of the present invention which display thrombospondin-like activity, compounds of the present invention can also be employed as intermediates in the synthesis of such useful compounds.

The compounds of the invention can be homopolymerized to themselves (i.e., (peptide)$_n$) or, heteropolymerized to one another (i.e., (peptide 1-peptide 2). The compounds can also be cyclized through disulfide or other means. The compounds can also be conjugated to biocompatible polymeric compounds, such as BIOPOL TM (W. R. Grace & Co.-Conn.)

While not wishing to be bound by any theory, it is believed that the compositions of the invention act as agonists or antagonists to native thrombospondin. These compounds are also believed to act as agonists or antagonists to circumsporozoite protein, thrombospondin related anonymous protein, and properdin complement protein. Further, since the compounds of the invention are small in size (relative to intact thrombospondin) the properties which they exhibit are more likely to be specific in nature, as opposed to the actions of other generally adhesive compounds such as RGD containing compounds (the sequence of which is found in over a hundred proteins) and fibronectin. The side effects of the peptide compounds of the invention are greatly reduced when compared with these broadly adhesive compounds.

D. Use

As stated previously, the compounds of the invention can be used in a variety of biological, prophylactic or therapeutic areas. It is contemplated that these compounds are useful in prevention or treatment of any disease state or conditions wherein thrombospondin-like activity plays a role. These disease states and conditions include, but are not limited to, metastasis, wound healing, atherosclerosis, malaria, thrombotic conditions, thrombolytic conditions, angiogenesis, cell proliferation, and complement activation. Antibodies directed against the compounds of the invention are also useful as diagnostic reagents, therapeutics, or carriers of other compounds.

Numerous in vitro and in vivo assays can be used to demonstrate compounds having thrombospondin-like activity. These assays include, but are not limited to, cell adhesion assays, platelet aggregation assays and cell proliferation assays.

Metastasis

Metastasis is the spread of disease from one part of the body to another unrelated to it, as in the transfer of the cells of a malignant tumor by way of the bloodstream or lymphatics. It is believed that metastasis is effected through a cascade mechanism which includes adhesion of tumor cells to endothelium, retraction of the endothelium, matrix degradation of the basement membrane and invasion of the tumor cells into the bloodstream. Intervention at any phase in this cascade could be beneficial to the treatment or prevention of metastatic cancers.

The native thrombospondin molecule has been shown to potentiate tumor cell metastasis (Tuszynski et al., *Cancer Research* (1987) 47:4130–4133). The mechanisms by which the thrombospondin potentiation occurs are not presently well understood.

Antimetastasis activity is characterized by the ability of the compounds to bind to melanoma cells in vitro (Tuszynski et al., *Anal. Bio.* (1990) 184:189–91), and the ability to reduce the size and number of tumor colonies in vivo (Tuszynski et al. *Cancer Research* (1987) 47:4130–4133).

The compounds of this invention are useful as antimetastatic agents, particularly useful as anti-pulmonary metastatic agents. These compounds inhibit the adhesion of metastatic tumor cells, particularly those which are responsive to thrombospondin. The compounds also reduce tumor colony number as well as tumor colony size.

There are a number of mechanisms by which such antimetastatic activity can be occurring. The peptides can be cytotoxic, or inhibit cell proliferation. As inhibitors of cell proliferation, the compounds can act to 1) inhibit mitogenesis, 2) inhibit angiogenesis, or 3) activate the complement pathway and the associated killer cells.

The compounds of the invention can also find use in biomedical devices. Since the compounds have the ability to promote the attachment of metastatic tumor cells, it is possible to coat a biomedical device with the compounds to effect the removal of circulating tumor cells from blood or lymph. The biomedical device is also useful to trap hepatomas.

Another use of the compounds is as a carrier to target toxins, drugs, hormones or imaging agents to metastatic tumor cells for diagnostic or therapeutic purposes. These carriers would also bind to hepatomas.

Wound Healing

Wound healing is the closure of wounds and can be divided into four essential components: inflammation, angiogenesis, collagen deposition and epithelialization. All four components play a role in the healing of wounds.

Wound healing activity is characterized by the ability of the compounds to show angiogenic activity, the ability of the compounds to stimulate collagen deposition and DNA synthesis in the in vivo sponge model or the ability of the compounds to improve wound healing or reduce healing time in an in vivo partial or full thickness wound model.

Atherosclerosis

Atherosclerosis is a disease state which is characterized by the deposition of small fatty nodules on the inner walls of the arteries, often accompanied by degeneration of the affected areas.

Atherosclerosis activity is characterized by the capacity of the compounds to inhibit the development of aortic lesions in rabbits fed a high cholesterol diet.

Malaria

Malaria is an infectious disease caused by any of various protozoans (genus Plasmodium) that are parasitic in the red blood corpuscles and are transmitted to mammals by the bite of an infected mosquito. The compounds of the invention can be used as antimalarial vaccines or as therapeutic agents to block cytoadherence.

Antimalarial activity is characterized by the ability to inhibit either the cytoadherence of malarial-infected red blood cells to endothelial cells, the malarial sporozoite recognition and entry into hepatocytes, or the malarial merozoite recognition and entry into red blood cells.

Thrombotic Conditions

The thrombotic activity associated with the compounds of the invention acts to inhibit platelet aggregation and platelet thrombus formation. Platelets participate in blood coagulation via binding fibrinogen, platelet aggregation and thrombus formation. As anti-thrombotics, these peptides can be useful in the following conditions: myocardial infarction, thromboembolic disease and thrombotic complications due to cancer and cardiovascular disease.

The compounds of this invention have the ability to specifically inhibit the second stage of platelet aggregation (i.e., the thrombospondin dependent stage of platelet aggregation). This activity allows the compounds to be useful in inhibiting thrombocytopenia caused as a result of disease state (i.e., Gray Platelet Syndrome, Essential Thrombocythemia, Myeloproliferative Syndrome) or induced by therapy (i.e., cancer therapy) or autoimmune diseases. These compounds also act to prevent coronary artery reocculsion following balloon catheterization The compounds of this invention modulate the formation and structure of blood clots. Thrombospondin is incorporated into fibrin clots and serves as a substrate for blood clotting Factor XIIIa. An IQQ sequence motif in thrombospondin has been implicated in cross-linking to factor XIIIa. Peptides containing IQQ modulate structure and formation of clots. Known fibrinolytic in vitro assays demonstrate this ability.

Antithrombotic activity is characterized by a number of assays, including 1) inhibition of ADP or thrombin-induced platelet aggregation in washed platelets; 2) inhibition of platelet aggregation in platelet-rich plasma; 3) inhibition of collagen induced platelet aggregation measured in vivo; and 4) inhibition of induced thrombus formation in a carotid artery—in this assay the peptide would delay or prevent occlusion of the artery following thrombus induction.

Alternatively, the compounds of the present invention are useful as potent clotting agents. The effect can be localized and is long lasting. This activity is useful when clotting is necessary (i.e., surgery or in hemophilia).

Thrombolytic Conditions

The thrombolytic activity associated with the compounds of the invention act to alter the structure of a formed thrombus, i.e., dissolution of a blood clot. Thrombolytic activity is characterized as the ability to enhance the dissolution of fibrin in the presence of plasmin (i.e., standard clot lysis assay).

Angiogenesis

Angiogenesis is the formation of blood and lymph vessels. The compounds of this invention are useful in the modulation of angiogenesis, particularly in enhancing wound healing, inhibiting or preventing tumor growth, diabetic retinopathy, and rheumatoid arthritis. Standard angiogenesis assays are well known in the art.

Complement Activity

The complement activity associated with the compounds of the invention can play a role in a variety of disease states. The peptides enhance complement-mediated clearance and inactivation mechanisms in both natural and acquired resistance to infection. The complement activity of the peptides serves to promote tumoricidal activity of the complement protein C3b. Additionally, complement proteins are known to contribute to reperfusion injury following heart attacks, and the compounds of the invention can inhibit such activity and are thus useful to lessen heart tissue death and tissue injury during a heart attack.

Antiviral

Viral infections involve attachment to cells of viral particles. The peptides of this invention interfere with viral attachment and are thus useful as antiviral agents.

Antibodies

Compounds of the present invention can also be used for preparing antisera for use in immunoassays employing labelled reagents, usually antibodies. Conveniently, the polypeptides can be conjugated to an antigen by means of dialdehydes, particularly from 4 to 6 carbon atoms and aliphatic, or carbodimide. These compounds and immunologic reagents may be labelled with a variety of labels such as chromophores, fluorophores such as, e.g., fluorescein or rhodamine, radioisotopes such as $^{125}I$, $^{35}S$, $^{14}C$, or $^{3}H$, or magnetized particles, by means well known in the art.

These labelled compounds and reagents, or labelled reagents capable of recognizing and specifically binding to them, can find use as, e.g., diagnostic reagents. Samples derived from biological specimens can be assayed for the presence or amount of substances having a common antigenic determinant with compounds of the present invention.

Thrombospondin levels are elevated in the serum of patients with metastatic breast and colon cancer (Tuszynski et al., *Antithrombotic Therapy* (1989) A28 and Smith et al., *American Association of Clinical Oncology* (in press)). Antibodies against the peptides of the invention can be useful as reagents in diagnostic/prognostic assays for various types of cancer, including but not limited to, gastrointestinal tract (gastric, colonic, and rectal) carcinomas, breast carcinomas and hepatic carcinomas.

In addition, monoclonal antibodies can be prepared by methods known in the art. The polyclonal and monoclonal antibodies can find therapeutic use in a number of cancer therapies. First, the antibodies can be used to sequester thrombospondin. This is useful since thrombospondin mediates tumor cell metastasis. Second, the antibodies can be used to block thrombospondin present on the tumor cell surface. Third, cytotoxic drugs, hormones, or imaging agents can be coupled to the antibodies for use in cancer therapy. Fourth, a biomedical device can be coated with the antibodies to remove excess thrombospondin from serum or the remove cells which bear thrombospondin on the cell surface.

The peptides of the invention can also be used to isolate thrombospondin cell surface receptors from extracts of cells or cell membranes. The thrombospondin cell surface receptors can be used to develop better thrombospondin analogs or to remove excess thrombospondin from serum.

The following examples are provided by way of illustration, rather than implying any limitation of the subject matter.

EXAMPLES

The peptides of this invention can be synthesized by conventional methods of peptide synthesis. A preferred method is the solid phase synthesis of Merrified, *J. Amer. Chem. Soc.* 85, 2149-2154 (1963); *Science* 150,178-185 (1965); Ibid. 232, 341-347 (1986). Solid phase synthesis is generally initiated from the C-terminal of the peptide by coupling a protected alpha amino acid to a suitable resin, e.g., phenylacetamidomethyl (PAM) polystyrene resin, or p-methylbenzhydrylamine (mBHA) resin when synthesizing a peptide with a C-terminal carboxyamide. In the present invention, the peptides were synthesized by solid-phase techniques performed on an Applied Biosystems 430A Peptide Synthesizer (Foster City, Calif.) using t-butyloxycarbonyl (t-Boc) alpha amino-group protected amino acids in accordance with the instructions of the manufacturer. During this synthesis, suitable amino acid side-chain protecting groups are used as needed. Thus, aspartic acid is protected on the beta-carboxyl group as the benzyl ester and arginine is protected on the guanidino group by tosyl. After the desired peptide has been synthesized, the peptide is cleaved from the resin and protecting groups are removed by treatment with a reagent such as hydrogen fluoride (HF). The peptide can then be purified by high performance liquid chromatography (HPLC) or other such methods of peptide purification. Background information on the established procedures for solid phase peptide synthesis can be found in "Solid Phase Peptide Synthesis" by Stewart and Young, W. H. Freeman & Co., San Francisco, 1969.

In accordance with the above description, the following procedures were used for the chemical synthesis of novel synthetic peptides:

Procedure A 0.1 mmole of selected Boc-AA$_n$-OCH$_2$-PAM Resin (0.2–0.8 mmole/g resin) (Applied Biosystems, Inc.) or p-mBHA Resin (0.2–0.7 mmole/g resin) (Applied Biosystems, Inc.) is treated according to Schedule A for the incorporation of the Boc-AA$_{n-1}$ or Boc-AA$_n$, respectively.

Schedule A. Small-scale Rapid Cycle Chemistry 1. 5-minute neat TFA wash
2. 40s DMF flow wash
3. 1-minute treatment with 20% DIEA in DMF
4. 40s DMF flow wash
5. Addition of 1–10 equivalents of preformed symmetric anhydride of a suitable protected t-boc amino acid dissolved in DMF
6. 10-minute coupling period
7. 40s DMF flow wash Procedure B 0.5 mmole of selected Boc-AA$_n$-OCH$_2$-PAM Resin (0.2–0.8 mmole/g resin) (Applied Biosystems, Inc.) or p-mBHA Resin (0.2–0.7 mmole/g resin) (Applied Biosystems.) is treated according to Schedule B for the incorporation of the Boc-AA$_{n-1}$ or BOC-AA$_n$, respectively.

Schedule B. Large-scale NMP/HOBT Chemistry 1. 3-minute wash with 30% TFA in DCM.
2. 17-minute wash with 50% TFA in DCM.
3. Wash 5× with DCM.
4. 1-minute wash with 5% DIEA in DCM.
5. 1-minute wash with 5% DIEA in NMP.
6. Wash 5× with NMP.
7. Addition of 1–4 equivalents of HOBT-ester of a suitably protected t-boc amino acid dissolved in NMP.
8. 30-minute coupling period.
9. Addition of DMSO to 20% and subsequent 16-minute coupling period.
10. Addition of 3.8 equivalents DIEA and subsequent 7-minute coupling period.
11. Wash 3× with DCM.
12. Wash with 10% acetic anhydride, 5% DIEA in DCM for 2 minutes.
13. Wash with 10% acetic anhydride in DCM for 4 minutes.
14. Wash 4× with DCM.

Example 1

Chemical Synthesis of WSPCSVTCG

Compound p1

Briefly, 0.13 grams of t-boc-Gly-OCH$_2$ PAM resin (0.79 mmol/g) was subjected to the following sequential addition of suitably protected amino acids: t-boc-Cys(4-CH$_3$Bzl), t-boc-Thr(Bzl), t-boc-Val, t-boc-Ser(Bzl), t-boc-Cys(4-CH$_3$Bzl), t-boc-Pro, t-boc-Ser(Bzl), and t-boc-Trp. Resultant, dry, N-terminal protected peptidyl-resin was suspended in anhydrous hydrogen fluoride containing 5% anisole, 5% dimethyl sulfide, and 1% p-thiocresol for two hours at −5° C. HF and volatile scavengers were removed with nitrogen sparge and the peptide-resin mixture was suspended in cold diethyl ether. The peptide-resin mixture was washed three times with diethyl ether, then the peptide was extracted with 30% acetic acid. This solution was diluted 1:1 with H$_2$O and lyophilized to afford the crude peptide. Purification was achieved on an Amicon C$_{18}$ MC-250-10 column utilizing reverse phase chromatography employing 0.1% aqueous trifluoroacetic acid with gradient generation afforded by the addition of 0.1% TFA in 90% acetonitrile and 10% H$_2$O. Fractions were collected and pooled based on a purity of 90%, as judged by analytical reverse-phase HPLC. Pooled fractions were diluted with deoxygenated H$_2$O and lyophilized to afford the pure peptide as a trifluoroacetic acid salt.

Example 2

Chemical Synthesis of WSPCSVTCG$_{NH2}$

Compound p6

Briefly, 0.17 g of p-methylbenzyhydrylamine resin (0.62 mmol/g) was subjected to the following sequential addition of suitably protected amino acids: t-boc-Gly, t-boc-Cys(4-CH$_3$Bzl), t-boc-Thr(Bzl), t-boc-Val, t-boc-Ser (Bzl), t-boc-Cys (4-CH$_3$Bzl), t-boc-Pro, t-boc-Ser (Bzl), t-boc-Trp (CHO). The resultant n-terminal deprotected, formylated peptidyl-resin was dried then suspended is anhydrous HF containing 8% anisole and 2% dimethyl sulfide. Treatment was for 0.5 hours at −20° C. and 2 hours at 0° C. The HF was removed with nitrogen sparge. The peptide-resin mixture was suspended in and washed 3 times with diethyl ether. The peptide was extracted with 25% acetic acid. The resin was washed with 50% acetic acid and with H$_2$O. The aqueous solutions were pooled, diluted 1:1 with deoxygenated H$_2$O and lyophilized to afford the formylated crude peptide. Deformylation was effected using the procedure described in Applied Biosystems 430A User Bulletin 18. (Apr. 28, 1987). The peptide (5 mg/ml concentrate) in 6M guanidine-HCl was cooled to 0° C. and ethanolamine added to 1M. The pH is lowered to 6 with concentrated hydrochloric acid.

Purification was on an Amicon C$_{18}$ MC-250-10 column using reserve-phase chromatography. The ratio of acetonitrile to H$_2$O was increased maintaining 0.1% TFA to achieve gradient elution. Collected fractions with a purity of 90%, as determined by analytical reverse-phase PHLC, were pooled, diluted with deoxygenated H$_2$O and lyophilized to afford pure peptide as a trifluoroacetic acid salt.

Example 3

Chemical Synthesis of fWSPCSVTCG$_{NH2}$

Compound p5

Briefly, procedure was same as for Example 2 except the deformylation step is not performed. The afforded crude peptide obtained past HF cleavage and subsequent lyophilization was purified as the formylated, C-terminal amide species.

Example 4

Other Thrombospondin Fragments or Analogs

Following the procedures outlined in Examples 1, 2 and 3 with appropriate modification, the following thrombospondin fragments or analogs were synthesized:

| Compound | Structure |
|---|---|
| p18 | W-D-I-C-S-V-T-C-G |
| P19 | W-S-S-C-S-V-T-C-G |
| p20 | W-T-S-C-S-T-S-C-G |
| p11 | W-S-P-W-S-E-W-T-S-C-S-T-S-C-G-N-G-I-Q-R-G-R |
| p17 | W-S-H-W-S-P-W-S-S-C-S-V-T-C-G-D-G-V-I-T-R-I-R |
| p12 | W-G-P-W-S-P-W-D-I-C-S-V-T-C-G-G-G-V-Q-K-R-S-R<br>W-S-P-C-S-V-T-C-S<br>W-S-Q-C-S-V-T-C-G<br>W-S-Q-C-N-V-T-C-G<br>W-T-P-C-S-V-T-C-G |
| p4 | D-G-G-W-S-H-W-S-P-W-S-S-C-S-V-T-C-G-D-G-V-I-T-<br>R-I-R-L-C-N-S-P-S-P-Q-M-N-G-K-P-C-E-G-E-A-R-E-T-<br>K-A-C-K-K-D-A-C-P-I-N-G-G |

Example 5

Direct Adhesion Assay

It is believed that thrombospondin acts in metastasis through its adhesive properties. An assay was developed, generally in accordance with the disclosure of Tuszynski et al. (*Anal. Bio.* (1990) 184:189–91) which evaluates the ability of melanoma cells to adhere to the thrombospondin fragments or analogs of the invention. In this assay, wells of a 96-well microtiter dish (Costar, Cambridge, Mass.) were incubated for two to three hours with 50 µl of a 40 µg/ml solution of various ligands in 20 mM NaCl, pH 7.3. Thrombospondin (purified by the method of Tuszynski et al., *J. Biol. Chem.* (1985) 260:12240–5), fibronectin (Sigma Chemical Co., Missouri) served as the positive control. Bovine serum albumin (BSA) (Sigma Chemical Co.) served as the negative control. Thrombospondin analogs of the invention p1, p5 and p6 were synthesized as described in Examples 1 through 3. Following peptide adhesion to the microtiter dish, the wells were aspirated, treated with 200 µl phosphate buffered saline (PBS) containing 1% BSA for 1 hour and then washed three more times with 200 µl PBS.

Mouse $B_{16}F_{10}$ melanoma cells were grown and harvested during log phase of growth using standard procedures. The harvested cells were washed two times in serum-free Dulbecco's minimum essential-medium (DMEM) (Flow Laboratories) and suspended in DMEM at a final concentration of $4 \times 10^5$ cells/ml. Of the cell suspension 100 µl was added to each well of the microtiter dish containing the various ligands and the dish incubated at 37° C. in a $CO_2$ incubator for 1 hour. Nonadherent cells were removed by aspiration and the wells washed three times with 200 µl of PBS. The total cell-associated protein was determined by dissolving the attached cells directly in the microtiter wells with 200 µl of the Pierce BCA working solution (*Pierce Chem. Co. Booklet* No. 23225 (1987)). The plate was covered with an adhesive mylar sheet (Flow Labs) and incubated at 60° C. for 30 minutes. Plates were allowed to cool to room temperature, cover sheets were removed, and the absorbance of each well was determined at 562 nm with a microtiter plate reader (Biotek, Burlington, Vt.)

The results shown in Table 1 indicate that the peptides of the inventions p1, p5, and p6 display adhesive properties.

TABLE 1

| Absorbed Compound (2 µg) | Adhesion as % Thrombospondin |
|---|---|
| Thrombospondin | 100 |
| p1 | 98 |
| p5 | 79 |
| p6 | 70 |
| BSA | 13 |

Example 6

Competitive Assay to Measure Thrombospondin Specific Adhesion to Melanoma Cells The direct adhesion assay of Example 5 was modified to measure the ability of the peptide compounds of the invention to compete with intact thrombospondin for adhesion to melanoma cells.

In this assay, intact thrombospondin is absorbed onto microtiter dishes as described in Example 5. The assay is similar to Example 5 except that before the melanoma cells are added to the microtiter dishes they are preincubated for 15 minutes with 100 µg/ml of various ligands.

The results shown in Table 2 indicate that peptide p1 is able to effectively compete with thrombospondin for adhesion of melanoma cells. Peptides p5 and p6 compete to a lesser degree at this concentration.

TABLE 2

| Compound | Concentration (µg/ml) | % of buffer control |
|---|---|---|
| buffer | — | 100 |
| p1 | 100 | 20 |
|  | 100 | 42 |
|  | 50 | 40 |
|  | 10 | 49 |
| p5 | 100 | 62 |
|  | 100 | 108 |
|  | 50 | 104 |
|  | 10 | 99 |
|  | 100 | 83 |
|  | 200 | 89 |
|  | 300 | 83 |
| p6 | 100 | 89 |
|  | 200 | 74 |
|  | 300 | 74 |

Example 7

Direct Platelet Adhesion Assay

The number of adherent platelets was essentially determined as previously described (Tuszynski et al., *Anal. Bio.* supra). Briefly, 100 µl of $5 \times 10^8$ platelets/ml washed as previously described (Tuszynski, et al., *Blood* 72, 109–225, 1988) were added to microtiter plates, the wells of which were treated with 50 µl of a 40 µg/ml peptide or protein solution (Hepes buffered saline, pH 7.4). Solutions were dried at room temperature after incubation in a fume hood for two hours. Wells were blocked for one hour with 1% BSA. Platelets (100 µl) were incubated in the wells for 30 minutes and nonadherent platelets were removed by aspiration. Wells were washed 3× with 200 µl of Hepes buffered saline, pH 7.4. The number of adherent platelets was determined by measuring the platelet-derived protein using the BCA protein assay.

The results shown in Table 3 indicate that at this concentration p1, p6, and to a lesser degree, p5 adhere to platelets.

TABLE 3

| Compound | Adherence as % Control |
|---|---|
| Thrombospondin | 100 |
| BSA | 0.7 |
| p1 | 39 |
| p5 | 2.1 |
| p6 | 38 |
| fibronectin | 83 |

Example 8

Competitive Assay to Measure Thrombospondin Specific Adhesion to Platelets

The direct adhesion assay of Example 7 was modified to measure the ability of the peptide compounds of the invention to compete with intact thrombospindin or fibronectin for adhesion of platelets.

In this assay, thrombospondin (TSP) or fibronectin (FN) was absorbed onto microtiter dish as described in Example 7. The assay was similar to Example 7 except that before platelets were added to the microtiter dishes they were preincubated with 250 μg/ml of various ligands.

The results shown in Table 4 indicate that peptide p1 effectively competed with thrombospondin for platelet adhesion, but did not compete with fibronectin.

TABLE 4

| Compound | Concentration (μg/ml) | Absorbed Protein | % Buffer Control |
|---|---|---|---|
| buffer | — | TSP | 100 |
| p1 | 250 | TSP | 71 |
| p5 | 250 | TSP | 107 |
| p6 | 250 | TSP | 98 |
| buffer | — | FN | 100 |
| p1 | 250 | FN | 108 |
| P5 | 250 | FN | 109 |
| p6 | 250 | FN | 96 |

Example 9

Platelet Aggregation Assay

Platelet aggregation was monitored on a single-channel aggregometer equipped to measure luminescence (Chromo-Log, Havertown, Pennsylvania). Platelet-rich-plasma (PRP) was obtained from whole blood anti-coagulated with 0.38% Sodium Citrate by centrifugation at 150×g for 20 minutes. Peptides were added to 0.5 ml of PRP and aggregation initiated with 1 μM ADP. Buffer blanks contained diluent (water) but no peptide.

The results shown in FIG. 1 indicate that p1, p5 and p6 inhibit platelet aggregation.

Example 10

Antimetastatic Activity In Vivo

The in vivo model used to demonstrate the antimetastatic activity of the peptide compounds of the invention is described by Tuszynski et al. (Cancer Res. (1987) 47:4130–4133). Briefly, C57 black mice were intravenously injected with $5 \times 10^5$ $B_{16}F_{10}$ mouse melanoma cells in the presence of either control buffer (Hepes buffered saline, pH 7.4), or the indicated amount of peptide compound of the invention p1, p5 or p6. After 16 days, the mice were sacrificed and the number of lung tumors counted.

The results shown in Table 5 indicate the peptides of the invention have antimetastatic activity. The p1-, p5- and p6-treated animals developed statistically fewer tumors than controls. Additionally, the lung tumors were smaller in size in the p1- and p6-treated animals.

TABLE 5

| Compound | Concentration μg/mouse | % buffer control |
|---|---|---|
| buffer | — | 100 |
| p1 | 30 | 49 |
| p5 | 30 | 87 |
| p6 | 30 | 91 |
| p6 | 100 | 102 |
| p6 | 300 | 50 |

What is claimed is:

1. A method for inhibiting thrombotic activity comprising administering to a host in need of such inhibition an effective amount of a polypeptide compound capable of inhibiting thrombotic activity and having the formula:

$$Z_1-AA_2-AA_3-AA_4-AA_5-AA_6-AA_7-AA_8-AA_9-Z_2$$

wherein:
$Z_1$ is hydrogen, amino, acetyl or up to nine amino acid residues;
$AA_1$ is tryptophan or n-formyl-tryptophan;
$AA_2$ is serine, threonine or aspartic acid;
$AA_3$ is proline, glutamic acid, serine or isoleucine;
$AA_4$ is cysteine;
$AA_5$ is serine or asparagine;
$AA_6$ is valine or threonine;
$AA_7$ is threonine or serine;
$AA_8$ is cysteine;
$AA_9$ is glycine or serine; and
$Z_2$ is hydroxyl, carboxyl, a non-amino acid or up to forty-two amino acid residues.

2. The method of claim 1 wherein said polypeptide compound is selected from the group consisting of:

D-G-G-W-S-H-W-S-P-W-S-S-C-S-V-T-C-G-D-G-V-I-T-R-I-R-L-C-N-S-P-S-P-Q-M-N-G-K-P-C-E-G-E-A-R-E-T-K-A-C-K-K-D-A-C-P-I-N-G-G.

3. The method of claim 1 wherein said amount is effective for inhibiting platelet aggregation.

4. The method of claim 3 wherein said amount is effective for inhibiting the thrombospondin-dependent second stage of platelet aggregation.

5. The method of claim 1 wherein said amount is effective for inhibiting thrombus formation.

6. The method of claim 1 wherein said amount is effective for inhibiting the formation of blood clots.

7. The method of claim 1 wherein said non-amino acid is agmatine.

8. The method of claim 1 wherein said up to forty-two amino acid residues are carboxyamide or alkylamide forms thereof.

9. A method for inhibiting thrombotic activity comprising administering to a host in need of such inhibition an effective amount of a polypeptide compound capable of inhibiting thrombotic activity which is selected from the group consisting of:
W-S-P-C-S-V-T-C-G,
fW-S-P-C-S-V-T-C-G-NH$_2$ and
W-S-P-C-S-V-T-C-G-NH$_2$.

* * * * *